(12) United States Patent
Feller, III et al.

(10) Patent No.: US 7,875,044 B2
(45) Date of Patent: Jan. 25, 2011

(54) REMODELING DEVICE FOR ANEURYSMS

(75) Inventors: Frederick Feller, III, Maple Grove, MN (US); Donald K. Jones, Dripping Springs, TX (US); Darren R. Sherman, Fort Lauderdale, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 726 days.

(21) Appl. No.: 11/663,489

(22) PCT Filed: Oct. 14, 2005

(86) PCT No.: PCT/US2005/036982

§ 371 (c)(1),
(2), (4) Date: Mar. 22, 2007

(87) PCT Pub. No.: WO2006/044632

PCT Pub. Date: Apr. 27, 2006

(65) Prior Publication Data

US 2008/0161936 A1     Jul. 3, 2008

Related U.S. Application Data

(60) Provisional application No. 60/619,493, filed on Oct. 15, 2004.

(51) Int. Cl.
*A61B 17/08* (2006.01)
(52) U.S. Cl. ..................................................... 606/157

(58) Field of Classification Search ................. 606/108, 606/151, 157, 159, 200, 191–198; 623/1.11–1.12
See application file for complete search history.

(56) References Cited

U.S. PATENT DOCUMENTS

| 5,895,410 | A | 4/1999 | Forber |
| 6,221,086 | B1 * | 4/2001 | Forber .................. 606/151 |
| 6,726,701 | B2 * | 4/2004 | Gilson et al. .......... 606/200 |
| 6,936,055 | B1 * | 8/2005 | Ken et al. .............. 606/157 |
| 2004/0068314 | A1 | 4/2004 | Jones |
| 2004/0098094 | A1 * | 5/2004 | Boyle et al. ........... 623/1.13 |

FOREIGN PATENT DOCUMENTS

| WO | WO 9902092 A1 | 1/1999 |
| WO | WO 9912484 A1 | 3/1999 |
| WO | WO 03049600 A2 | 6/2003 |

OTHER PUBLICATIONS

EP 05812021 Search Report dated Oct. 26, 2009.

\* cited by examiner

*Primary Examiner*—Kevin T Truong

(57) ABSTRACT

A method of occluding a defect in the wall of a body vessel is provided. An outlet portion of a microcatheter is delivered to the defect, then at least a body portion of a thin film occlusion device is radially expanded from a collapsed orientation to a deployed orientation for engaging the microcatheter and covering at least a portion of the defect. Thereafter, an embolic media is released into the defect from the microcatheter for facilitating thrombosis. The body portion of the occlusion device is substantially porous in the collapsed orientation, but substantially non-porous in the deployed orientation for preventing prolapse of the embolic media into the body vessel.

25 Claims, 2 Drawing Sheets

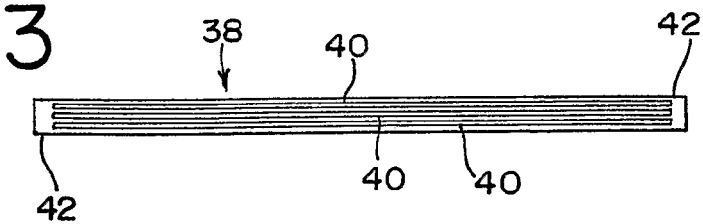
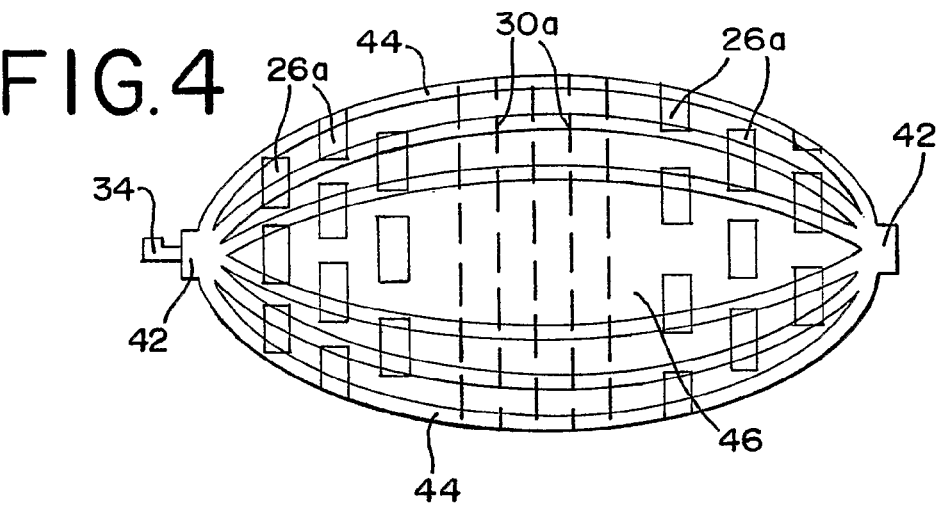
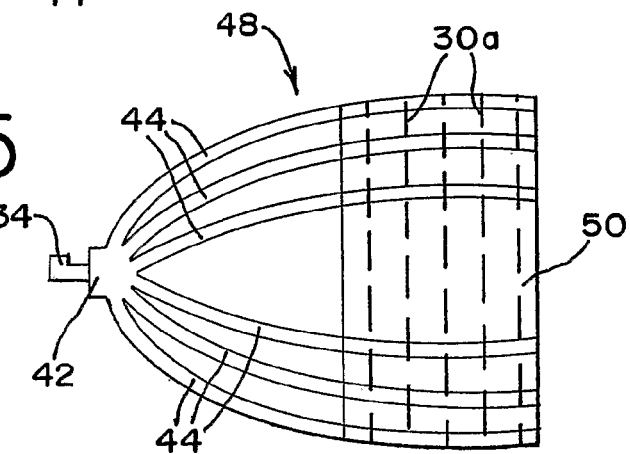
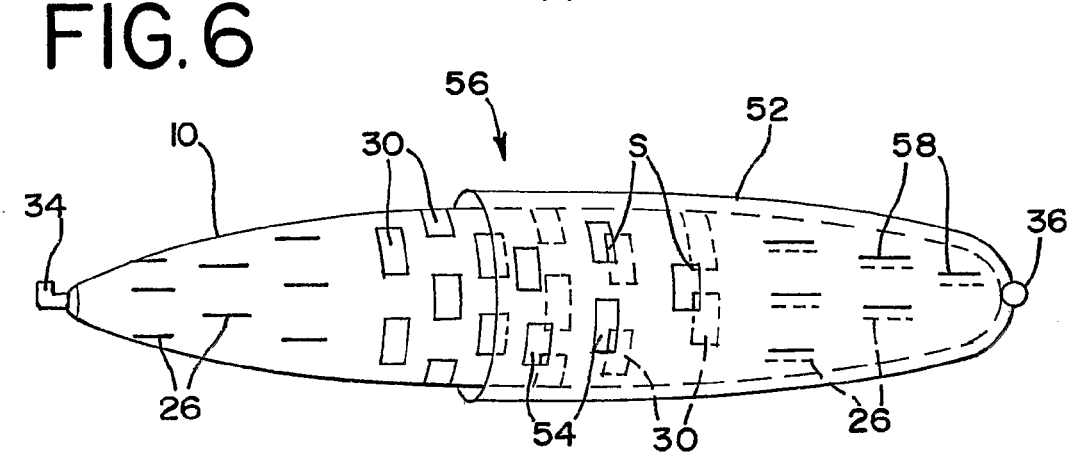

REMODELING DEVICE FOR ANEURYSMS

CROSS REFERENCE TO RELATED APPLICATION

This application claims priority from provisional patent application Ser. No. 60/619,493, filed Oct. 15, 2004, which is hereby incorporated herein by reference.

FIELD OF THE INVENTION

This invention generally relates to methods and medical devices for use in treating defective or diseased body vessels.

DESCRIPTION OF RELATED ART

An aneurysm is an abnormal bulge or ballooning of the wall of a blood vessel, which most commonly occurs in arterial blood vessels. Aneurysms typically form at a weakened point of a wall of a blood vessel. The force of the blood pressure against the weakened wall causes the wall to abnormally bulge or balloon outwardly. Aneurysms, particularly cranial aneurysms, are a serious medical condition because an aneurysm can apply undesired pressure to areas within the brain. Additionally, there is the possibility that the aneurysm may rupture or burst leading to serious medical complications including mortality.

When a patient is diagnosed with an unruptured aneurysm, the aneurysm is treated in an attempt to prevent the aneurysm from rupturing. Unruptured aneurysms have traditionally been treated by what is known as "clipping." Clipping requires an invasive surgical procedure wherein the surgeon makes incisions into the patient's body to access the afflicted blood vessel. Once the surgeon has accessed the aneurysm, he or she places a clip around the neck of the aneurysm to block the flow of blood into the aneurysm which prevents the aneurysm from rupturing. While clipping may be an acceptable treatment for some aneurysms, there is a considerable amount of risk involved with employing the clipping procedure to treat cranial aneurysms because such procedures require open brain surgery.

More recently, intravascular catheter techniques have been used to treat cranial aneurysms because such techniques do not require cranial or skull incisions, i.e., these techniques do not require open brain surgery. Typically, these techniques involve using a catheter to deliver embolic devices to a preselected location within the vasculature. For example, in the case of a cranial aneurysm, methods and procedure, which are well known in the art, are used for inserting the distal end of a delivery catheter into the vasculature of a patient and guiding the catheter through the vasculature to the site of the cranial aneurysm. An embolic device is then attached to the end of a pusher member which pushes the embolic device through the catheter and out of the distal end of the catheter where the embolic device is delivered into the aneurysm.

Once the embolic device has been deployed within the aneurysm, the blood clots on the embolic device and forms a thrombus. The thrombus forms an occlusion which seals off the aneurysm, preventing further ballooning or rupture. The deployment procedure is repeated until the desired number of embolic devices is deployed within the aneurysm. Typically, it is desired to deploy enough embolic devices to obtain a packing density of about 20% or more, preferably about 35% and more if possible.

The most common embolic device is an embolic coil. Embolic coils are typically constructed from a metal wire which has been twisted into a helical shape. One of the drawbacks of embolic coils is that they may migrate from the diseased site and prolapse into a surrounding vessel lumen, especially if the coils are delivered to an aneurysm having a relatively large neck opening. Furthermore, overpacking of an aneurysm can also cause some coils to escape into the adjacent body vessel. The coils may then partially or completely occlude the parent vessel, which can result in a number of well-known maladies.

One known method of preventing such prolapse is to use a stent or similar occlusion device in conjunction with the embolic media. For example, U.S. Pat. No. 5,795,331 (Cragg et al.); U.S. Pat. No. 5,916,235 (Guglielmi); U.S. Pat. No. 5,928,260 (Chin et al.); U.S. Pat. No. 5,951,599 (McCrory); U.S. Pat. No. 6,626,928 (Raymond et al.) and U.S. Patent Application Publication No. 2004/0111112 (Hoffmann) describe various approaches and are hereby incorporated herein by reference. Generally, an occlusion device is delivered to the parent vessel adjacent to the aneurysm or diseased site, along with a catheter for delivering the embolic media. According to one approach, the occlusion device may then be expanded to plug the aneurysm neck while the distal end of the catheter is within the aneurysm, thereby pinching the catheter in place and preventing prolapse when the embolic devices are thereafter released. Alternatively, the occlusion device may be provided with open pores overlaying the aneurysm neck, in which case the occlusion device is expanded and the distal end of the catheter is passed through a pore to communicate with the interior of the aneurysm.

A problem to be addressed is to provide an occlusion device with portions having reversible porosities that can be delivered endoluminally in surgical applications, while implanting and locating same at the proper site of an occlusion, wherein the porosities reverse in order to provide an at least generally closed portion with an immediate occlusive function to "plug" the vessel defect and control or stop blood flow into the diseased site and an at least generally open portion which allows blood flow at other areas around the diseased site.

Accordingly, a general aspect or object of the present invention is to provide an occlusion device having portions with varying porosity properties which separately perform a plugging function and a filtration or fixation function upon deployment at or near a diseased site.

Another aspect or object of this invention is to provide an improved occlusion device that incorporates thin film metal deposition technology in preparing occlusion devices which exhibit regions of opposing porosity during deployment, which porosity is substantially reversed when properly positioned for occlusion.

Another aspect or object of this invention is to provide a method for plugging a vessel defect while delivering embolic material to the defect.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with the present invention, an occlusion device is provided that has a thin film structure that has a contracted or collapsed orientation which facilitates endoluminal deployment as well as an expanded or deployed orientation within the body.

Porosity is provided in at least a first portion of the occlusion device in the radially contracted orientation in the form of pores that are generally open when the device is stretched longitudinally. These pores close substantially or fully upon deployment, when the thin film device longitudinally foreshortens and expands radially to shrink the pores to a smaller profile. This pore closure upon expansion provides a substantially non-porous barrier to cover a vessel defect and at least partially prevent blood flow thereto.

In contrast to these pores, an area having opposing porosity may be provided in at least a second portion of the occlusion device. When the term "opposing porosity" is used herein, this refers to an area having pores that are generally closed when the device is in a collapsed orientation for delivery. These pores open upon implantation when the device is deployed to a target occlusion site and expanded. These pores allow for continued passage of blood flow through the parent vessel while occluding the diseased location. Hence; it will be understood that these two pore areas can be considered to essentially reverse porosities upon deployment, moving from open to closed and vice versa when implanted within the body.

The occlusion device is delivered to the target site, along with a microcatheter capable of deploying embolic material. When used herein, the terms "embolic material" and "embolic media" and "embolic devices" are intended to be interchangeable and refer to an apparatus or substance which may be deployed to the vasculature for promoting blood clotting and the formation of an embolus or thrombus. An outlet portion at a distal end of the microcatheter is fed into the vessel defect, then the occlusion device is expanded in order to plug the defect opening and engage at least a portion of the microcatheter. Thereafter, the embolic material is released into the defect, while at least a portion of the occlusion device prevents the embolic material from prolapsing into the parent vessel. Finally, the microcatheter and occlusion device may be removed from the body when the embolic material has been successfully deployed.

Special application for the present invention has been found for treating aneurysms in the neurovascular system or the peripheral vasculature. However, it will be seen that the products and methods described herein are not limited to particular medical devices or methods of manufacture or particular surgical applications.

BRIEF DESCRIPTION OF THE DRAWINGS

FIG. 3 is a front elevational view of a tube used to form support struts of an alternative embodiment of the occlusion device;

FIG. 4 is a front elevational view of the occlusion device of FIG. 2, with a support structure according to an alternative embodiment;

FIG. 5 is a front elevational view of another alternative embodiment of an occlusion device according to the present invention; and FIG. 6 is a front elevational view of an occlusion device in a collapsed configuration according to an alternative embodiment, with portions broken away for clarity.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

Figure 1:
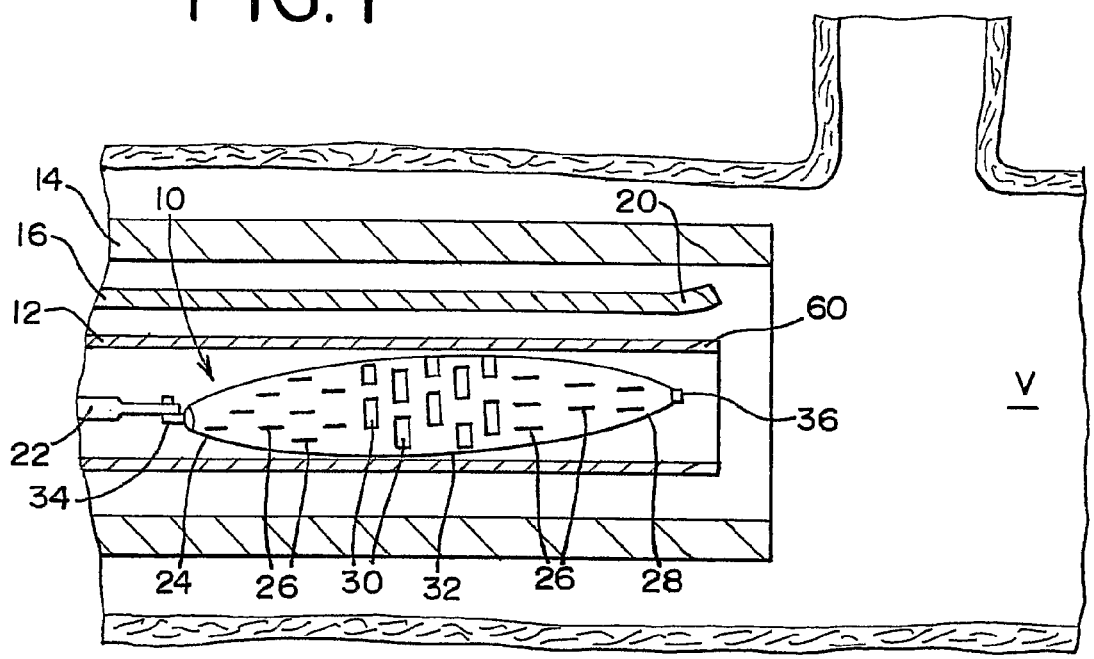
FIG. 1 is a front elevational view of a microcatheter and an occlusion device according to the present invention, in a delivery configuration.

FIG. 1 illustrates an occlusion device 10 in a collapsed orientation within a delivery catheter 12. The delivery catheter 12 is carried by a gliding catheter 14, which is configured to also carry a microcatheter 16. The microcatheter 16 carries one or more embolic devices or media 18, which can be deployed to a diseased section of the vasculature, such as into an aneurysm, as seen in FIG. 2.

Figure 2:
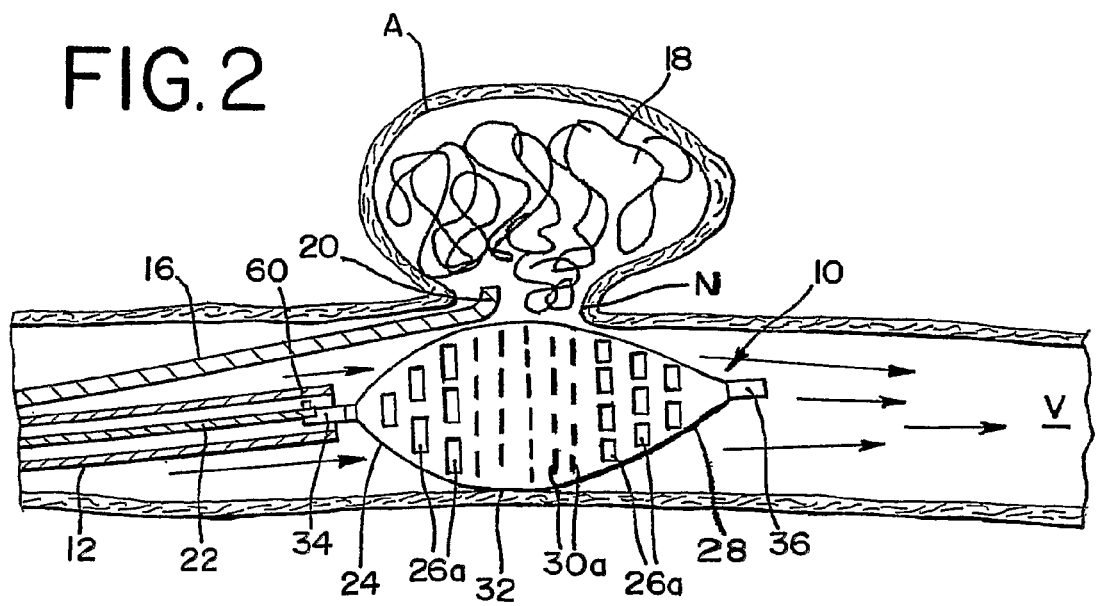
FIG. 2 is a front elevational view of the microcatheter and occlusion device of FIG. 1 in a deployed configuration.

FIG. 2 shows occlusion device 10 in an expanded or deployed position within a body vessel V, while embolic media 18 and an outlet portion 20 of microcatheter 16 are positioned within an aneurysm A associated with body vessel V. Also illustrated in FIGS. 1 and 2 is a positioning member 22 associated with a proximal end portion 24 of the occlusion device 10.

The occlusion device 10 preferably comprises a thin film mesh formed by physical vapor deposition onto a core or mandrel. Such deposition techniques are well-known to those skilled in the art. Most preferably, a thin film of nitinol, or other material which preferably has the ability to take on a shape that had been imparted to it during manufacture, is formed. When nitinol material is used in forming the thin film, the thin film can be at the martensite state. In addition, the thin film when made of nitinol or materials having similar shape memory properties may be austenite with a transition from martensite to austenite, typically when the device is raised to approximately human body temperature, or in the range of about 95 F. to 100 F.

In making the thin film mesh, the selected material is preferably sputter-deposited onto a core, which core is then typically removed by chemical etching or the like. Examples of this type of deposition are found in US Published Patent Application No. 2003/0018381, No. 2004/0098094 and No. 2005/0033418, which are hereby incorporated herein by reference. Nitinol, which encompasses alloys of nickel and titanium, is a preferred film material because of its superelastic and shape memory properties, but other known biocompatible compositions with similar characteristics may also be used.

The thickness of the thin film mesh depends on the film material selected, the intended use of the device, the support structure, and other factors. A thin film of nitinol is preferably between about 0.1 and 250 microns thick and typically between about 1 and 30 microns thick. More preferably, the thickness of the thin film mesh is between about 1 and 10 microns or at least about 0.1 micron but less than about 5 microns. A supported mesh may be thinner than a self-supported mesh.

In the collapsed orientation of FIG. 1, the occlusion device 10 includes a plurality of generally longitudinal slits 26 disposed along end portions 24 and 28 which are substantially closed and non-porous, while a set of slots 30 located along a body portion 30 between the end portions 24 and 28 are substantially open and porous. The slits 26 and slots 30 may be formed by any known means, but are preferably formed using laser-cutting.

The illustrated slots 30 are shown in FIG. 1 with generally identical rectangular openings which are arranged in a uniform pattern along the body portion 32, but they may assume other open profiles, e.g., diamond-shaped openings, and be arranged randomly or in selected non-uniform patterns, depending on the intended use. The slits 26 may also assume differing profiles, e.g., curvilinear, and be arranged randomly or in selected non-uniform patterns, according to the intended use.

In use, the slits 26 and slots 30 assist in allowing the associated portions of the occlusion device 10 to expand radially. For example, FIG. 2 shows the occlusion device 10 when same assumes a deployed or expanded orientation within body vessel V. Compared to the collapsed orientation of FIG. 1, the occlusion device 10 in the deployed orientation is longitudinally foreshortened and radially expanded. When implanted in the body, the occlusion device 10 moves from the elongated, collapsed orientation of FIG. 1 to the foreshortened, deployed orientation of FIG. 2, while the slits move from the generally closed condition 26 of FIG. 1 to the generally open condition 26a of FIG. 2. Compared to the generally closed condition 26, the slits in the open condition 26a resemble the open slots 30 of FIG. 1, but they may assume other open profiles, such as diamond-shaped openings, depending on their initial closed profile. In this open condition 26a, the slits provide an increased porosity and are intended to allow the continued flow of blood and other bodily fluids through the parent vessel V, as represented by the arrows in FIG. 2.

In contrast to the slits 26, the slots move from the generally open condition of FIG. 1 to the generally closed condition 30a of FIG. 2 when the occlusion device has been deployed to the target area. In short, the slots 26 telescope to cause longitudinal foreshortening and radial expansion, whereas the slits 26 are compressed by the force of the occlusion device moving to its deployed orientation, causing them to narrow and open. Thus, it will be appreciated that both the slits 26 and slots 30 contribute to the longitudinal foreshortening and radial expansion of the associated portions of the occlusion device 10. In the generally closed condition 30a, the slots generally resemble the closed slits 26 of FIG. 1, but they are generally disposed transversely or circumferentially about body portion 32.

Of course, the slots may assume other closed profiles, depending on their initial open profile. In this generally closed condition 30a, the slots provide a decreased porosity and are intended to prevent or reduce the flow of blood and other bodily fluids into the aneurysm A, thereby fostering thrombosis and occlusion therewithin. Furthermore, the generally closed slots 30a are also sized and configured to prevent any embolic media 18 from migrating into the vessel V from the interior of the aneurysm A.

The occlusion device 10 preferably includes a proximal end 24 having a shape that is generally closed, which can culminate in a plasma weld and include an engagement member 34, and a distal end 28 of a shape that is generally closed and that is atraumatically sealed shut by a plasma weld 36 or other suitable seal. If the occlusion device includes engagement member 34, as illustrated in FIGS. 1 and 2, the device can be removed from the body or readjusted within the vessel V after deployment, according to methods which are well-known to those skilled in the art.

In an alternative embodiment, the occlusion device 10 may be provided without end portions 24 and 28, such that it resembles a sleeve or a stent that generally conforms to the above description of the body portion 32. This embodiment provides the important functions of facilitating blood flow through the parent vessel V, while occluding the neck N of aneurysm A, but is less preferred because it is more difficult to reposition and remove without engagement member 34.

According to another alternative embodiment, the occlusion device 10 is provided with only proximal end portion 24 and body portion 32. This embodiment is preferred over the one previously described, because it may include an engagement member 34, which interacts with the positioning member 22 to facilitate removal and repositioning of the occlusion device 10.

The configuration of the device 10 as deployed in FIG. 2 is typically achieved by heating a nitinol thin film mesh or other shape memory material when on a shaping core or mandrel until it reaches an austenite condition, whereby it is heat-set into the desired shape. This set shape can be offset when cooled and removed from the mandrel and stretched down to a configuration such as shown in FIG. 1. Alternatively, rather than providing a mesh which moves into a deployed configuration upon heating, a mesh can be provided with a shape memory material that will automatically return to its collapsed configuration upon heating.

Typically, such memory "setting" is adequate to achieve the desired expanded shape of the device. It can be possible to assist this expanded shaping by varying slot or slit size, shape, and location. For example, the elasticity of the mesh can be supplemented in the end portions 24 and 28 adjacent to the body portion 32 by overlaying those portions with relatively long slits that open to allow for enhanced radial expansion when the occlusion device 10 moves from a collapsed orientation to a deployed orientation. In contrast, less radial expansion is desired adjacent to the hook 34 and plasma weld 36, so shorter slits that open to a lesser extent may be used. Alternatively, if even less radial expansion is required, selected regions may be devoid of slits and slots, which means that the amount of expansion which results is due to the characteristics of the thin film material unaided by slots or slits in the material. However, this approach is less preferred because it can impede blood flow through the parent vessel V near the engagement member 34 and plasma weld 36.

According to an alternative embodiment of the present invention, the described occlusion devices may be provided with a support structure, similar to that described in U.S. Pat. No. 6,428,558 (Jones and Mitelberg), which is hereby incorporated herein by reference. FIG. 3 shows a generally hollow tube 38 which may be used to make an internal support structure for an occlusion device as illustrated in FIG. 4. The tube 38 is preferably comprised of nitinol or another shape memory material having a wall between about 70 and 250 microns thick, most preferably between about 175 and 225 microns thick. The tube 38 generally also has at least one region with a plurality of longitudinal cuts 40 (FIG. 3) and two uncut end portions 42.

In assembling the tube 38, a compressive force is applied to the end portions 42 of the tube 38 until the cuts 40 buckle outwardly to define the struts 44 of FIG. 4. A thin film mesh 46, as illustrated in FIG. 4, may thereafter be laid over the struts 44 and sealed at least along the end portions 42. Alternatively, the tube 38 may be returned to the configuration of FIG. 3 and inserted into the thin film mesh 46 before the sealing step. In another embodiment, the thin film mesh 46 can be positioned inside the tube 38 to provide a device having an external support structure. As a further option, the tube can be positioned between thin film mesh layers to provide an occlusion device having an encapsulated support structure.

The mesh 46 is preferably a biocompatible, flexible material and may be thinner than the thin film of FIGS. 1-2, because it is not required to support itself. The mesh 46 does include a pore structure similar to the self-supporting embodiments, whereby the slots move to a generally closed condition and the slits move to a generally open condition when the occlusion device is deployed, as illustrated in FIG. 4. It will be appreciated that, while this aspect of the present invention is shown and described with reference to the occlusion device of FIG. 2, the shape and configuration of the cuts along the tube can be varied so that it can be applied to other occlusion devices according to the present invention. For example, if there is only one end portion 42, then a wide opening will form at the opposite end portion, as seen in the occlusion device 48 of FIG. 5. In the embodiment of FIG. 5, the mesh 50 is associated with only the portion of the struts 44 which will overlay the aneurysm neck N in a deployed orientation. Of course, the mesh 50 may be extended to be associated with the entirety of the struts 44, provided that the mesh associated with the portion of the struts 44 adjacent to the end portion 42 includes slits which move to a generally open condition when deployed.

According to another alternative embodiment of the present invention, the described occlusion devices may be created with an additional outer thin film layer 52, as illustrated in FIG. 6. An occlusion device 10 according to FIG. 1 is nested within a thin film layer 52, which is partially broken away in FIG. 6. These layers 10 and 52 operate according to the principles described above. Preferably the two layers 10 and 52 have differing slot patterns or at least slot patterns that are out of phase with each other, such that the slots 30 of the inner layer 10 are misaligned with the slots 54 of the outer layer 52, thereby decreasing the effective slot size S of the layered occlusion device 56. As a result, the layered occlusion device 56 will have substantially the same radially expansive properties according to the present invention, while providing an even lower porosity along the body portion in the deployed orientation, which improves the occlusive properties. This embodiment is useful when cutting technology does not provide slot sizing as small as may be desired in some circumstances, such as when using an embolic gel, which is apt to prolapse into the parent vessel if the slots along the body portion of the occlusion device are not sufficiently closed in the deployed orientation.

Unless the slits 26 of the inner layer 10 are substantially aligned with the slits 58 of the outer layer 52, the effective open slit size along the end portions will be diminished in the deployed configuration. Typically, this diminishment will not be complete and blood flow therethrough, even though diminished, can supply the parent vessel with blood flow, oxygen, and the like to maintain it in a healthy condition during the procedure. However, as illustrated in FIG. 6, the outer and inner slits 26 and 58 are preferably generally aligned and most preferably the outer slits 58 directly overlay the inner slits 26.

In another embodiment of the device, substantially the same effect of FIG. 6 may be achieved using an outer layer having only longitudinal slits. Some slits of the outer layer can be aligned with those slits of the inner layer which are to be open in a deployed configuration, while other slits of the outer layer are generally out of phase or misaligned with the slots of the inner layer, which are to be closed in a deployed configuration. Accordingly, in a deployed configuration, the aligned slits of the respective two layers will define openings, while the misaligned slits of the outer layer and slots of the inner layer will be generally closed. It will be seen that the inner layer may also be provided with only longitudinal slits, and substantially the same pattern of alignment and misalignment may be practiced in order to define open and closed portions of the deployed device. The exclusive use of slits may be preferred in some instances where it is difficult to provide adequate slots for the collapsed orientation.

In yet another alternative embodiment of the occlusion device of FIG. 6, the outer layer may cover less than the entirety of the inner layer. For example, the outer layer may only include the slotted body portion, which has the effect of decreasing the deployed porosity of that portion, without the concern of properly aligning the inner and outer slits, as is required of the device of FIG. 6.

Preferably, the provided microcatheter 16 and embolic material 18 have a construction and operation according to known devices. However, the nature of the embolic material 18 will affect the construction of the occlusion device 10, because the porosity of the body portion 32 when deployed must be lower for certain embolic media, such as gels, than for others, such as coils. It is more difficult to form small pore openings than large pore openings, so accordingly, it is preferred to use embolic coils due to their resistance to prolapsing through larger pore openings. On the other hand, the nature of the occlusion device 10 will effect the selection of the proper microcatheter 16. As will be understood with reference to FIG. 2, embolic material 18 is ejected from the microcatheter 16 into the aneurysm A after the occlusion device 10 has fully expanded, so it is important that an appropriate microcatheter 16 is selected so that it is not deformed to the point of closure by the compressive force applied to it by the expanded occlusion device 10.

The occlusion device 10 and microcatheter 16 are preferably configured and sized for concurrent transport within a guiding catheter 14. The occlusion device 10 is delivered in the collapsed configuration of FIG. 1 and is preferably carried at a downstream end 60 of a delivery catheter 12 which is movable within guiding catheter 14. When the guiding catheter 14 has been moved into a position generally adjacent to the diseased area, the outlet portion 20 of the microcatheter 16 is placed into communication with the vessel V by axial movement of the microcatheter 16 with respect to the guiding catheter 14. Thereafter, as shown in FIG. 2, outlet portion 20 is fed into the interior of the aneurysm A through the neck N and the downstream end 60 of the delivery catheter 12 may be moved outside of the guiding catheter 14 by axial movement of the two catheters 12 and 14 with respect to each other.

When the outlet portion 20 of the microcatheter 16 has been properly positioned within the aneurysm A, the downstream end 60 of the delivery catheter 12 is positioned adjacent to the aneurysm A and then positioning member 22 at least partially ejects the occlusion device 10 into the target region. This may be achieved by moving the positioning member 22 distally, moving the delivery catheter 12 in a retrograde direction, or a combination of both types of movement. The positioning member 22 remains connected to the engagement member 34, so the occlusion device 10 may be repositioned after it has been partially and/or fully ejected from the delivery catheter 12.

Preferably, the occlusion device 10 is comprised of a shape memory material, such as nitinol, which will move to the deployed configuration of FIG. 2 upon exposure to living body temperatures. In moving to the deployed orientation, the slits 26 of the end portions 24 and 28 move to a generally open condition 26a, as described previously, which causes the end portions 24 and 28 to radially expand to at least partially engage the walls of the vessel V, which prevents the occlusion device 10 from moving away from the aneurysm neck N. The open slits 26a define a generally open flow path, which allows blood to continue flowing through the vessel V.

While the slits move from a generally closed condition 26 to a generally open condition 26a, the slots along the body portion 32 move from the generally open condition 30 of FIG. 1 to the generally closed condition 30a of FIG. 2, which causes the body portion 32 to longitudinally foreshorten and radially expand. As illustrated in FIG. 2, the occlusion device 10 is preferably configured such that the body portion 32 radially expands until it overlays substantially the entire neck N of the aneurysm A and engages at least a portion of the microcatheter 16. In this position, the body portion 32 acts as a barrier that, depending on the porosity of the slots in their generally closed condition 30a, either prevents or at least decreases the flow of blood into the aneurysm A, which promotes thrombosis, even before embolic material 18 is introduced.

When the neck N has been substantially closed, embolic material 18 is ejected from the microcatheter 16 into the aneurysm A. As the embolic material 18 is being deposited in the aneurysm A, there is the risk that it can prolapse into the vessel V before it has been sufficiently packed, but the body portion 32 and generally closed slots 30a combine to act as a barrier that prevents the embolic material 18 from migrating into the vessel V during the packing process.

When a sufficient amount of embolic material 18 has been deposited within the aneurysm A, such that the risk of prolapse is substantially eliminated, the occlusion device 10 may be returned to its collapsed orientation and removed from the body, along with the positioning member 22, microcatheter 16, delivery catheter 12, and guiding catheter 14. Alternatively, if it is desired to maintain the occlusion device 10 within the vessel V for a longer period of time, then it can be detached from the positioning member 22 and left in place, while the positioning member 22, microcatheter 16, delivery catheter 12, and guiding catheter 14 are removed from the body.

It will be understood that the exact order of the steps of the above-described process are not critical and may be varied according to user preference. For example, the delivery catheter 12 may be moved outside of guiding catheter 14 before the microcatheter 16 or the two catheters 12 and 16 may be moved away from the guiding catheter 14 at substantially the same time. Similarly, the occlusion device 10 may be ejected into the vessel V and moved into position before the outlet portion 20 of the microcatheter 16 is moved into the aneurysm A. Furthermore, if the occlusion device 10 is not formed of a self-expanding material, then it can be partially expanded using known techniques, e.g., the application of internal pressure, before the microcatheter 16 is finally placed and the occlusion device 10 is fully expanded.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A method of occluding at least a portion of a defect in a wall of a body vessel, comprising:
providing a microcatheter capable of deploying an embolic material;
providing a delivery catheter housing an occlusion device in a collapsed orientation, wherein the occlusion device comprises a thin film mesh including: a proximal end portion associated with a body portion, a plurality of slot members associated with said body portion, and a plurality of slit members associated with said proximal end portion, wherein said slot members are in a generally open condition and said slit members are in a generally closed condition when the occlusion device is in said collapsed orientation;
positioning at least an outlet portion of said microcatheter at the defect;
ejecting at least a portion of the occlusion device from a downstream end of the delivery catheter;
positioning the occlusion device adjacent to the defect;
providing for radial expansion of the occlusion device to a deployed orientation within the body vessel at which said slot members are in a generally closed condition and said slit members are in a generally open condition and such that a body portion of the occlusion device at least partially covers the defect and engages at least a portion of the microcatheter; and
ejecting said embolic material into the defect from said outlet portion of the microcatheter.

2. The method of claim 1, wherein said providing of an occlusion device provides a support structure for supporting at least one of said proximal end portions and said body portion.

3. The method of claim 1, wherein said providing of an occlusion device provides a distal end portion associated with said body portion, having a substantially closed end configuration, and having a plurality of slit members in a generally closed condition when the occlusion device is in said collapsed orientation and in a generally open condition with radial expansion movement of the occlusion device to said deployed orientation within the body vessel.

4. The method of claim 1, further including longitudinally foreshortening and radially expanding at least the portions of said occlusion device associated with said slot members and said slit members upon movement of the occlusion device to the deployed orientation.

5. The method of claim 1, wherein said providing of the occlusion device provides the body portion and proximal end portion of the occlusion device of a material having shape memory properties.

6. The method of claim 5, wherein the material having shape memory properties is nitinol.

7. The method of claim 6, wherein the nitinol is a martensite thin film.

8. The method of claim 6, wherein the nitinol is an austenite thin film that transitions from martensite to austenite upon exposure to human body temperature.

9. The method of claim 1, further including providing the slot members in said generally closed condition and configuring the body portion of the occlusion device to prevent the embolic material from prolapsing into the body vessel.

10. A method of occluding at least a portion of a defect in a wall of a body vessel, comprising:
providing a microcatheter capable of deploying an embolic material;
providing an occlusion device in a collapsed orientation, the occlusion device comprising a thin film mesh including a proximal end portion and a distal end portion associated with a body portion, and wherein said body portion is substantially porous and said proximal end portion and said distal end portion are substantially non-porous in said collapsed orientation and said body portion is substantially non-porous and said proximal end portion and said distal end portion are substantially porous in said deployed orientation;

positioning at least an outlet portion of the microcatheter at the defect;

positioning the occlusion device adjacent to the defect;

radially expanding the occlusion device to a deployed orientation, such that a body portion of the occlusion device at least partially covers the defect and engages at least a portion of the microcatheter; and ejecting the embolic material into the defect from said outlet portion of the microcatheter.

11. The method of claim 10, further including providing the body portion, proximal end portion and distal end portion of the occlusion device of a material having shape memory properties.

12. The method of claim 11, wherein the material having shape memory properties is nitinol.

13. The method of claim 12, wherein the nitinol is a martensite thin film.

14. The method of claim 12, wherein the nitinol is an austenite thin film that transitions from martensite to austenite upon exposure to human body temperature.

15. A system for occluding at least a portion of a defect in a wall of a body vessel, comprising:

a microcatheter capable of deploying an embolic material to the defect; and an occlusion device capable of moving from a collapsed orientation to a deployed orientation, wherein said occlusion device comprises a thin film mesh including:

a body portion engageable with at least a portion of the defect and at least a portion of the microcatheter when the occlusion device is in said deployed orientation, and a plurality of slot members associated with said body portion, wherein said slot members are in a generally open condition when the occlusion device is in said collapsed orientation and said slot members are in a generally closed condition with radial expansion movement and longitudinal foreshortening movement of the occlusion device to said deployed orientation within the body vessel.

16. The system of claim 15, wherein said occlusion device further comprises a proximal end portion associated with said body portion and a plurality of slit members associated with said proximal end portion, wherein said slit members are in a generally closed condition when the occlusion device is in said collapsed orientation and said slit members are in a generally open condition with radial expansion movement and longitudinal foreshortening movement of the occlusion device to said deployed orientation within the body vessel.

17. The system of claim 15, wherein said occlusion device further comprises an engagement member associated with said proximal end portion for selective removal of the occlusion device from a body vessel or repositioning of the occlusion device in a body vessel.

18. The system of claim 15, wherein said occlusion device further comprises a distal end portion associated with said body portion, having a substantially closed end configuration, and having a plurality of slit members associated with said distal end portion, wherein said slit members are in a generally closed condition when the occlusion device is in said collapsed orientation and said slit members are in a generally open condition with radial expansion movement and longitudinal foreshortening movement of the occlusion device to said deployed orientation within the body vessel.

19. The system of claim 15, wherein said occlusion device further comprises a support structure for supporting at least said body portion.

20. The system of claim 15, wherein said occlusion device further comprises a plurality of thin film layers, at least one of said layers having a plurality of slit members, at least one of said layers having a plurality of slot members, and at least some of said slits of one of said film layers are not in full alignment with any slot of another of said film layers.

21. The system of claim 15, wherein said body portion of the occlusion device is comprised of a material having shape memory properties.

22. The system of claim 21, wherein said material having shape memory properties is nitinol.

23. The system of claim 22, wherein said nitinol is a martensite thin film.

24. The system of claim 22, wherein said nitinol is an austenite thin film that transitions from martensite to austenite upon exposure to human body temperature.

25. The system of claim 15, wherein said body portion of the occlusion device is comprised of a material having a thickness greater than about 0.1 microns and less than about 5 microns.

* * * * *